United States Patent [19]

Dosmann

[11] Patent Number: 5,449,898

[45] Date of Patent: Sep. 12, 1995

[54] HIGH SPATIAL RESOLUTION AREA ARRAY DETECTION READHEAD WITH A REDUCED SAMPLE DETECTION AREA AND METHOD FOR USING THE SAME

[75] Inventor: Andrew J. Dosmann, Granger, Ind.

[73] Assignee: Miles Inc., Elkhart, Ind.

[21] Appl. No.: 273,263

[22] Filed: Jun. 30, 1994

[51] Int. Cl.⁶ .............................................. H01J 40/14
[52] U.S. Cl. .................................. 250/208.1; 250/234; 359/211
[58] Field of Search ...................... 250/208.1, 234, 235, 250/236; 359/211, 669; 348/202

[56] References Cited

U.S. PATENT DOCUMENTS 4,241,257 12/1980 Koester ................................. 359/211
4,637,692 1/1987 Baluteau et al. .................... 359/211

Primary Examiner—David C. Nelms
Assistant Examiner—Que T. Le
Attorney, Agent, or Firm—Jerome L. Jeffers

[57] ABSTRACT

The high spatial resolution area array detection readhead and method for using the same involve modifying an existing area array detection readhead to provide improved spatial resolution within the sample detection area. One modification involves reducing the field of view of the area array detection readhead. The reduction in the field of view increases pixel spatial resolution because the same number of pixels in the area array detector cover a smaller area. This reduction can be achieved by changing the magnification of the lens of the area array detection readhead or by moving the sample detection area closer to the area array detection readhead. The next modification involves properly aligning the reduced field of view within the sample detection area to take advantage of the improved pixel resolution. Preferably, by rotating the typical area array detection readhead 90 degrees with respect to the sample detection area, the length of the reduced field of view aligns with the width of the sample detection area. Finally, an optical wedge is positioned between the area array detection readhead and the sample detection area. The optical wedge is designed to shift the reduced field of view a predetermined number, X, of degrees from normal along the length of the sample detection area to cover a first field of the sample detection area. By inverting the optical wedge or introducing another optical wedge, the field of view is shifted −X degrees from normal and fills the remaining field of the sample detection area. As such, the sample detection area is divided into two fields that cover the entire sample detection area. Accordingly, by switching the optical wedge between the two wedge positions, the improved area array detection readhead shifts the reduced field of view + and −X degrees to image the entire sample detection area at the higher spatial resolution.

27 Claims, 2 Drawing Sheets

HIGH SPATIAL RESOLUTION AREA ARRAY DETECTION READHEAD WITH A REDUCED SAMPLE DETECTION AREA AND METHOD FOR USING THE SAME

FIELD OF THE INVENTION

The present invention generally relates to the field of clinical chemistry. More particularly, the present invention relates to an improved area array detection readhead having high spatial resolution that analyzes the color change associated with one or more test areas on a test strip following contact thereof with a liquid specimen, such as urine or blood.

BACKGROUND OF THE INVENTION

Reagent test strips are widely used in the field of clinical chemistry. A test strip usually has one or more test areas, and each test area is capable of undergoing a color change in response to contact with a liquid specimen. The liquid specimen usually contains one or more constituents or properties of interest. The presence and concentrations of these constituents of interest in the specimen are determinable by an analysis of the color changes undergone by the test strip. Usually, this analysis involves a color comparison between the test area or test pad and a color standard or scale. In this way, reagent test strips assist physicians in diagnosing the existence of diseases and other health problems.

Color comparisons made with the naked eye can lead to imprecise measurement. Today, strip reading instruments employ a variety of area array detection readheads utilizing CCD (charge-coupled device), CID (charge-injection device) or PMOS detection structures for detecting color changes to the test strips. These instruments accurately determine the color change of a test strip but sometimes fail to measure minute color inconsistencies due to the limited spatial resolution for a given sample detection area or field of view. For example, a 739×484 pixel array with a fixed field of view equal to 4"×3" results in a fixed pixel spatial resolution equal to 0.0062"×0.0054" (based on a pixel size of 9.92 $\mu m \times 8.66$ $\mu m$). Area array detection readheads having resolutions in this range can fail to detect minute color variations (i.e. Non Hemolyzed Trace detection of Occult Blood reagent, etc.) on the image of a MULTISTIX ® reagent strip of the type sold by Miles Inc., Diagnostics Division, of Elkhart, Ind. 46515. After the urine specimen contacts the test pad of a MULTISTIX ® reagent strip, intact blood cells appear as tiny green blotches on the yellow test area. The area array detection readhead can miss the minute color variation caused by an individual blood cell due to the cell's very small size. Unfortunately, area arrays detection readheads having higher spatial resolutions which can detect minute color variations cost considerably more and are less reliable. Therefore, a need exists for new area array detection system which provides improved spatial resolution without a significant increase in cost or risk.

Most area array detection readheads are designed to work with video camera systems which conform to broadcast television standards, and thus the spatial dimensions (L×W) of the area arrays in the detection readheads are proportional to the 4×3 aspect ratio of television picture tubes. Area array detection readheads typically use area arrays having the 4×3 aspect ratio to lower cost and risk. Typically, the area array detection readhead has a lens that images a fixed sample detection area or field of view (the example above used a 4"×3" area) onto an area array having a 4×3 aspect ratio (i.e. 6.4 mm×4.8 mm). The present invention takes advantage of the lower cost and risk associated with current area array detectors and provides improved spatial resolution.

SUMMARY OF THE INVENTION

The present invention involves modifying an existing area array detection readhead to provide improved spatial resolution within the sample detection area. One modification involves reducing the field of view of the area array detection readhead to less than the original sample detection area. The reduction in the field of view increases pixel spatial resolution because the same number of pixels in the area array detector cover a smaller area. For example, a 4"×3" sample detection area can be reduced to 3"×2.25." This reduction can be achieved by changing the magnification of the lens of the area array detection readhead or by moving the sample detection area closer to the area array detection readhead. The next modification involves properly aligning the reduced field of view within the sample detection area to take advantage of the improved pixel resolution. Preferably, by rotating the typical area array detection readhead 90 degrees with respect to the sample detection area the length of the reduced field of view aligns with the width of the sample detection area. Using the example, the 3" length of the reduced field of view aligns with the 3" width of the sample detection area, and the 2.25" width of the field of view aligns with the middle 2.25" of the 4" length of the sample detection area.

The improved area array detection readhead utilizes an optical wedge positioned between the area array detection readhead and the sample detection area. The optical wedge is designed with the proper slope relative to the sample detection area to shift the reduced field of view a predetermined number, X, of degrees from normal along the length of the sample detection area to cover a first field of the sample detection area. The selected shifting angle for the field of view and thus the angle for the optical wedge depends on a number of factors such as the type of area array detector, the magnification of the lens, the size of the field of view, the desired spatial resolution, the size of the sample detection area, the size of the area array, the distance from the sample detection area, etc. Using the example, the optical wedge shifts the 3"×2.25" field of view to cover a 3"×2.25" portion or field of the 4"×3" sample detection area. Furthermore, by inverting the optical wedge or introducing another optical wedge, the field of view is shifted to cover the remaining field of the sample detection area. As such, the sample detection area is divided into two fields that cover the entire sample detection area. Accordingly, by switching or inverting the optical wedge, the improved area array detection readhead shifts the reduced field of view to image the entire sample detection area at the higher spatial resolution. In this way, the improved area array detection readhead improves the spatial resolution of prior area array detection readheads by utilizing more pixels per surface area.

BRIEF DESCRIPTION OF THE DRAWINGS

The advantages of the present invention will become apparent upon reading the following detailed description and upon reference to the accompanying drawings in which.

DETAILED DESCRIPTION OF THE PREFERRED EMBODIMENTS

Figure 1:
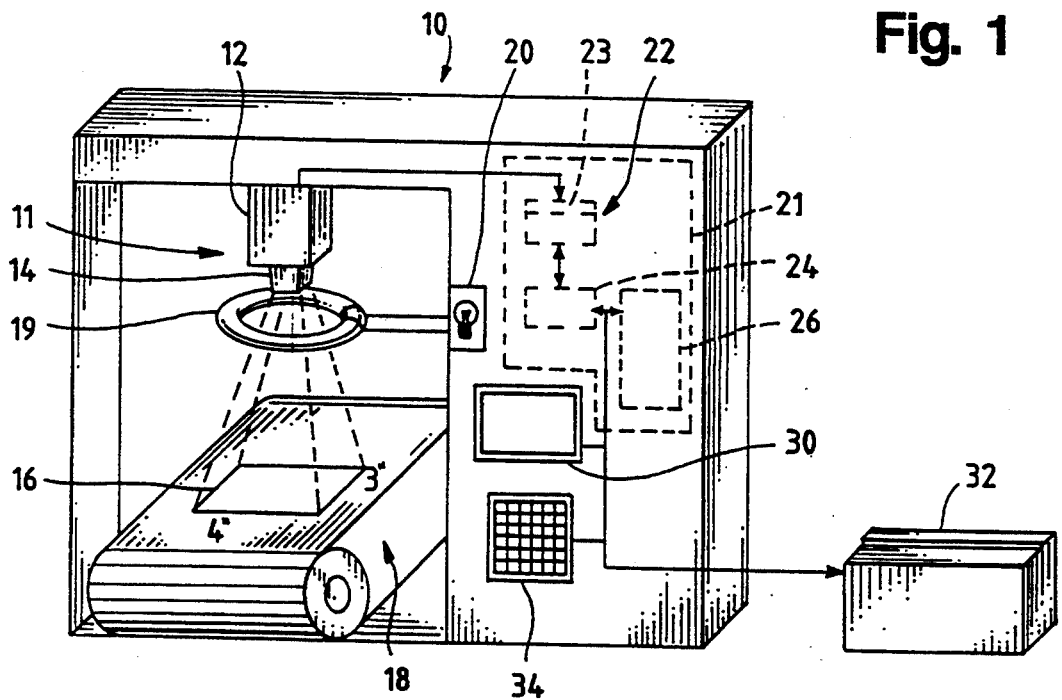
FIG. 1 shows a prior art embodiment of a test sample detector utilizing an area array detection readhead.

Referring now to the drawings, and more particularly to FIG. 1, there is illustrated an existing test sample detector, generally designated by the reference numeral 10. The test sample detector 10 utilizes an area array detection readhead 11 that includes an area array detector 12 and a lens 14. The area array detection readhead 11 views a sample detection area 16 through the lens 14 which focuses an image of the sample detection area 16 onto the area array of the area array detector 12. The test sample detector 10 analyzes test samples within the sample detection area 16. In the preferred embodiment, reagent test strips are placed in the sample detection area 16, either manually or by a transport mechanism 18. Each test strip has test pads reacted with the test samples containing constituents of interest. The test pads change color when reacted with the liquid test samples containing constituents of interest. By analyzing the color of the test pads, the concentration or presence of a constituent of interest can be determined as well as other measurable properties of the liquid specimen such as color or specific gravity.

The area array detection readhead 11 can include such conventional area array detection readheads as CCD cameras (i.e. color, monochrome or monochrome with color filters), CID cameras or transistor arrays (i.e. PMOS detection structures). The test sample detector 10 can be a video test strip reader as described in U.S. application Ser. No. 08/117,782, now U.S. Pat. No. 5,408,535, herein incorporated by reference. For purposes of a general description of the test sample detector 10, the area array detection readhead 11 produces an analog signal representing an image of the sample detection area 16. Typically, an illumination source 19 illuminates the sample detection area 16, and the illumination source 19 should evenly illuminate the sample detection area 16 in order for the area array detection readhead 11 to accurately measure the color or reflectance of the test samples on the sample detection area 16. This illumination source 19 is shown in FIG. 1 as a fiber optic illumination ring connected to a stabilized source 20.

The test sample detector 10 of FIG. 1 is illustrated with conventional processing and control circuitry 21 coupled to the area array detection readhead 11. The processing and control circuitry 21 receives the analog signals from the area array detection readhead 11 and processes these signals to analyze the test-samples. The processing and control circuitry can include an image handler 22 conventionally coupled to the area array detection readhead 11. The image handler 22 usually includes a signal converter 23 that converts or digitizes the analog signal from the area array detection readhead 11 into a digital signal representing the image. Typically, the image handler 22 also stores the image represented by the digital signal in a manner that enables a processor 24 to effectively process the digital information. Alternatively, the area array detection readhead can include a signal converter to produce a digital signal to the image handler.

The processor 24 is conventionally coupled to the image handler 22. The processor 24 is preferably a Digital Signal Processor (DSP) on a dedicated board that analyzes the image of the sample detection area 16 represented by digital information. The processor 24 is coupled to a memory 26, for storing analysis data, instructions and calculation results. Moreover, the processor 24 is conventionally coupled to a display 30 and/or a printing mechanism 32 for displaying the test results and a keypad 34 to enable user interaction with the test sample detector 10. The test sample detector 10 can also include a co-processor (not shown) for performing calculations or controlling the transport mechanism 18 and a secondary storage (not shown), such as disk storage.

For discussion purposes, the area array detection readhead 11 of FIG. 1 conforms to broadcast television standards, and thus the dimensions (L×W) for the area array (not shown) of the area array detector 12 are proportional to the 4×3 aspect ratio seen on television picture tubes. As such, the lens 14 of the area array detection readhead 11 focuses a fixed field of view or sample detection area 16 (the above example uses a 4"×3" field of view) 16 onto the area arrays (not shown) of the area array detector 12 which has a 4×3 aspect ratio (assuming fixed size pixels). A typical size for the area array is 6.4 mm×4.8 mm. To remain consistent with the above example and for ease of understanding, the area array detection readhead 11 has a fixed field of view equal to 4"×3" which, at this point, is the sample detection area 16. Moreover, the area array detector 12 has a 739×484 pixel array resulting in a fixed pixel resolution of 0.0054 inches of sample detection area/pixel x 0.0062 inches of sample detection area/pixel. This resolution is based on an area army with a size of 6.4 mm×4.8 mm and a fixed pixel size of 8.66 microns×9.92 microns.

Figure 2:
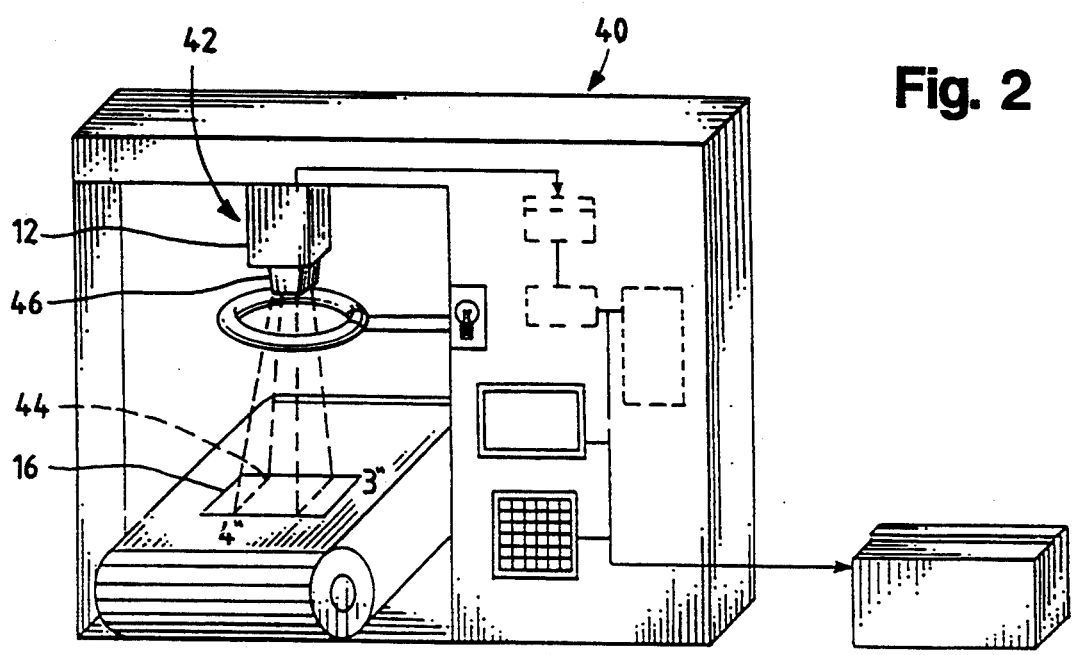
FIG. 2 shows a test sample detector utilizing an area array detection readhead with a reduced field of view which has been rotated 90 degrees in accordance with the improved area array detection readhead of the present invention.

In the preferred embodiment, several modifications of the known test sample detector 10 are required to achieve improved spatial resolution within the same sample detection area 16. FIG. 2 illustrates a modified test sample detector 40 which has a reduced field of view covering slightly over half of the sample detection area 16. As mentioned above, the original field of view was the same size as the sample detection area 16. In accordance with the preferred embodiment, the field of view of the area array detection readhead 42 is reduced to approximately half of the original field of view. Reducing the field of view by approximately one half increases the pixel spatial resolution by 78% because the same number of pixels in the area array of the detector 12 cover a smaller area (i.e., the reduced field of view). In the example, the 4"×3" field of view is reduced to 3"×2.25". This can be accomplished by changing the lens 14 of FIG. 1 to a lens 46 with a stronger magnification or by moving the sample detection area 16 closer to the area array detection readhead 42.

To obtain the preferred configuration for the reduced field of view 44 illustrated in FIG. 2, the area array detector 12 of FIG. 1 must be modified by rotating the area array detector 12 90 degrees with respect to the 4"×3" sample detection area 16. As can be seen in FIG. 2, this orientation positions the reduced field of view 44 in the middle of the sample detection area 16. Moreover, using the example, the 3" length of the reduced field of view 44 aligns with the 3" width of the sample detection area 16. At this point, the area array detection readhead 42 has an improved spatial resolution in the field of view 44 but only covers a little over half of the sample detection area 16.

Figure 3:
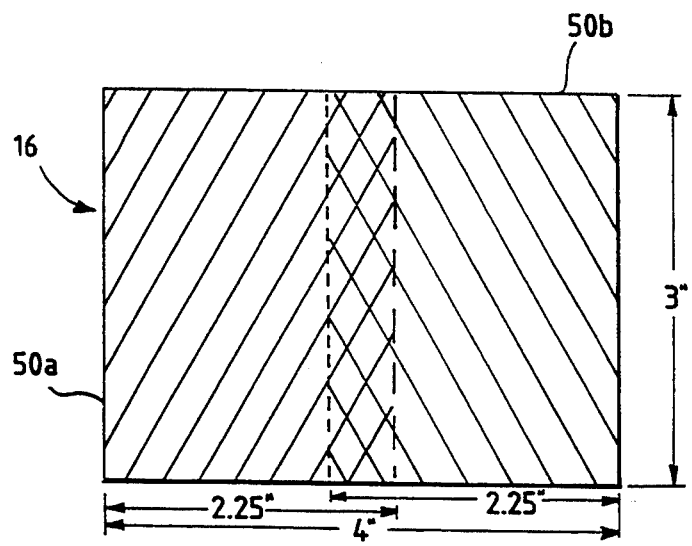
FIG. 3 shows an image of the sample detection area divided into two fields.

The present invention involves shifting the reduced field of view 44 by + and − a predetermined number of degrees, X, from normal along the length of the sample detection area 16. In this way, the improved area array detection readhead scans the entire sample detection area 16 with the reduced field of view 44 with an improved spatial resolution. According to the example described for the preferred embodiment of the present invention, the field of view 44 is shifted + and − about 17 degrees from normal along the length of the sample detection area 16 to detect the entire 4"×3" sample detection area 16. As shown in FIG. 3, shifting the field of view + and − 17 degrees divides the sample detection area 16 into two fields 50a and 50b. The two fields 50a and 50b lie side by side in the sample detection area 16, and although not required, the two fields 50a and 50b are shown overlapping in the middle of the sample detection area 16. By way of the example, the dimensions for each of the two fields 50a and 50b is the same as the reduced field of view, 3"×2.25", and the dimensions for the sample detection area 16 is 4"×3".

Figure 4:
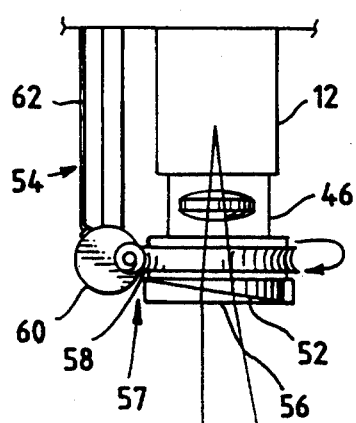
FIG. 4 shows a side view of an improved area array detection readhead utilizing an optical wedge in a first position to shift the field of view a predetermined number, X of, degrees from normal on the sample detection area.
Figure 4:
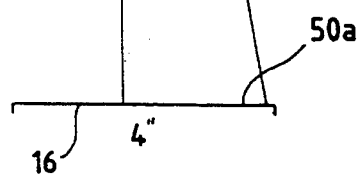

The preferred embodiment of the present invention uses an optical wedge to shift the reduced field of view 44 by + and − a predetermined number of degrees, X, from normal along the length of the sample detection area 16. In a first position the optical wedge shifts the field of view +X degrees. FIG. 4 shows an improved area array detection readhead 54 that utilizes approximately a 9.5 degree optical wedge 52 positioned between the lens 46 of the area array detection readhead 54 and the sample detection area 16 to shift the reduced field of view 44 (FIG. 2) approximately +17 degrees to cover the field 50a of the sample detection area 16. The determination of a shifting angle and the angle for the optical wedge depends on many factors, including the type of area array detector, the magnification of the lens, the size of the field of view, the desired spatial resolution, the size of the sample detection area, the size of the area array, and general physical specifications for the test sample detector. In this embodiment of the improved area array detection readhead 54, the optical wedge 52 is mounted within a wedge housing 56 that is preferably made of plastic. Moreover, the wedge housing 56 is moveably mounted relative to the lens 46 of the improved area array detection readhead 54.

The improved area array detection readhead uses a switching mechanism 57 engaging the optical wedge 52 to change the position of the optical wedge 52 relative to the lens 46 and the sample detection area 16 such that the entire sample detection area 16 is examined with the reduced field of view 44 (FIG. 2). In a preferred embodiment, the wedge housing 56 includes teeth 58 attached to or molded into the housing 56. The teeth 58 are preferably engaged by a motor 60 that is adjacent to the housing 56 and forces the rotation of the wedge housing 56 to change the position of the optical wedge 52 with respect to the lens 46. Preferably, the motor 60 should include at least one gear to engage the teeth 58 of the wedge housing 56.

After the test samples on the field 50a of the sample detection have been examined, a control signal is sent over a motor control line 62 that activates the motor 62. The motor 62 engages the wedge housing 56 and rotates the optical wedge 52 about 180 degrees from its current position to a second position. In the second position, the selected optical wedge 52 shifts the reduced field of view 44 (FIG. 2)−X degrees form normal along the 4" length of the sample detection area 14 to cover the other field 50b of the sample detection area 16. Using the approximately 9.5 degree optical wedge 52 of FIG. 4 in the second position, the optical wedge shifts the field of view 44 about −17 degrees from normal to cover the remainder of the sample detection area 16. As such, the improved area array detection readhead 54 examines test samples on the entire sample detector area 16 with improved spatial resolution at a low cost and high reliability.

Figure 5:
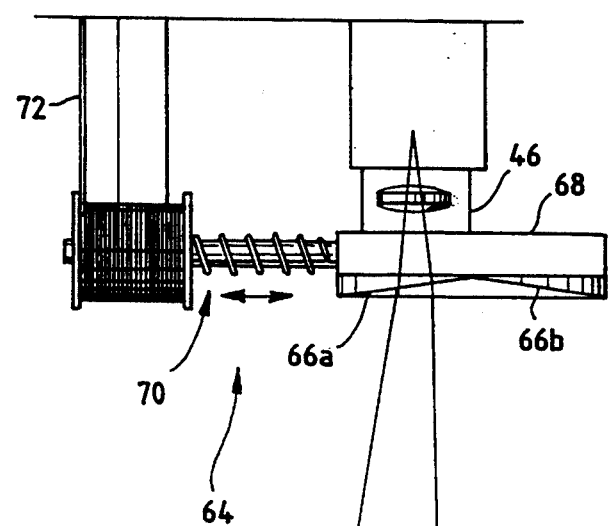
FIG. 5 shows a side view of another embodiment of an improved area array detection readhead with the optical wedge in a second position to shift the field of view X degrees from normal on the sample detection area.
Figure 5:
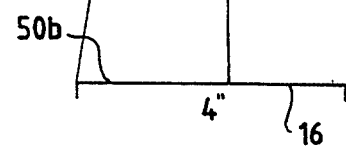

FIG. 5 shows another embodiment of an improved area array detection readhead 64 of the present invention with a field shifter using two optical wedges 66a and 66b. In FIG. 5, the optical wedge 66a shifts the reduced field of view 44 (FIG. 2) to cover the field 50b of the sample detection area 16. As in the above example, a 9.5 degree optical wedge 66a is positioned between the lens 46 and the sample detection area 16. The optical wedge 66a, however, is housed within a wedge housing 68 together with another optical wedge 66b symmetrically positioned opposite the wedge 66a. The wedge housing 68 is moveably mounted relative to the lens 46 of the improved area array detection readhead 64 to enable either the optical wedge 66a or 66b to be positioned between the lens 46 and the sample detection area 16. Preferably, the wedge housing 68 is adapted for engagement by a switching mechanism 70. The switching mechanism 70 is preferably mounted adjacent to the wedge housing 68 and engages the wedge housing 68 for changing the positions of the optical wedges 66a and 66b relative to the lens 46 and the sample detection area 16.

As shown in FIG. 5, the optical wedge 66a shifts the reduced field of view 44 (FIG. 2) about −17 degrees to cover the field 50b of the sample detection area 16. After the test samples on the field 50b have been examined, the reduced field of view 44 (FIG. 2) is shifted +17 degrees from normal along the 4" length of the sample detection area 16 to examine the test samples on the field 50a of the sample detection area 16. To accomplish this, a switching signal on a switching mechanism control line 72 activates the switching mechanism 70. The switching mechanism 70 changes the position of the wedge housing 68 such that optical wedge 66b is positioned between the lens 46 and the sample detection area 16. The switching 70 mechanism can include a motor, gear and teeth configuration (not shown) or a spring-loaded solenoid. In the case of the spring-loaded solenoid shown, the switching signal activates the solenoid to force the wedge housing 68 to a first position, and when the switching signal is interrupted, the solenoid is deactivated, thereby allowing the spring to force the wedge housing 68 to a second position. As the optical wedge 52 of FIG. 4, the optical wedge 66b shifts the reduced field of view 44 (FIG. 2) approximately +17 degrees from normal along the 4" length of the sample detection area 16 to cover the field 50a of the sample detection area 16. In this way, the improved area array detection readhead 64 analyzes test samples on the entire sample detection area 16 with improved spatial resolution.

The improved area array detection readhead of the present invention provides higher spatial resolution at low cost and low risk. The improved area array detection readhead involves cheap but effective modifications to existing area array detection readheads, including area array detection readheads utilizing CCD technology, CID technology, transistor arrays and other forms of photo-sensitive area arrays.

Thus, the improved area array detection readhead and method for providing improved spatial resolution and many of its attendant advantages will be understood from the foregoing description and various modifications may be made in the form, construction and arrangement of the parts thereof without departing from the spirit and scope of the invention or sacrificing all of its material advantages, the form described above being merely a preferred embodiment thereof.

I claim:

1. An improved area array detection readhead for examining test samples on a sample detection area, comprising:
    an area array detector imaging a reduced field of said sample detection area;
    an optical wedge positioned between said area array detector and said sample detection area to shift said reduced field on said sample detection area; and
    a switching mechanism for changing the position of said optical wedge relative to said area array detector and said sample detection area.

2. The improved area array detection readhead of claim 1 wherein said optical wedge being mounted within a wedge housing, said switching mechanism engaging said wedge housing.

3. The improved area array detection readhead of claim 2 wherein said switching mechanism including a motor engaging said wedge housing.

4. The improved area array detection readhead of claim 1 wherein said area array detector imaging said field through a lens positioned between said optical wedge and said area array detector.

5. The improved area array detection readhead of claim 1 wherein said area array detector utilizing CCD technology.

6. The improved area array detection readhead of claim 1 wherein said area array detector utilizing CID technology.

7. The improved area array detection readhead of claim 1 wherein said area array detector utilizing transistor array technology.

8. The improved area array detection readhead of claim 1 wherein said area array detector positioned such that a length of said reduced field of view aligning with said width of said sample detection area.

9. The improved area array detection readhead of claim 1 wherein said area array detector having an area array with a length and width proportional to about 4×3 and said sample detection having a length and width proportional to said length and width of said area array, said area array detector being positioned such that said length of said area array aligns with said width of said sample detection array and said field being reduced to slightly over half of said sample detection area.

10. An improved area array detection readhead for examining test samples on a sample detection area, comprising:
    an area array detector imaging a reduced field of said sample detection area;
    a field shifter positioned between said area array detector and said sample detection area to shift said field on said sample detection area, said field shifter including a first optical wedge and a second optical wedge; and
    a switching mechanism engaging said field shifter to change the positioning of said first and second optical wedges relative to said area array detector and said sample detection area.

11. The improved area array detection readhead of claim 10 wherein said first and second optical wedges being mounted within a wedge housing, said switching mechanism engaging said wedge housing.

12. The improved area array detection readhead of claim 11 wherein said switching mechanism including a motor engaging said wedge housing.

13. The improved area array detection readhead of claim 11 wherein said switching mechanism including a spring-loaded solenoid engaging said wedge housing.

14. The improved area array detection readhead of claim 10 wherein said area array detector imaging said field through a lens positioned between said optical wedge and said area array detector.

15. The improved area array detection readhead of claim 11 wherein said area array detector utilizing CCD technology.

16. The improved area array detection readhead of claim 10 wherein said area array detector utilizing CID technology.

17. The improved area array detection readhead of claim 10 wherein said area array detector utilizing transistor array technology.

18. The improved area array detection readhead of claim 10 wherein said first optical wedge positioned symetrically opposite said second optical wedge.

19. The improved area array detection readhead of claim 10 wherein said area array detector positioned such that a length of said reduced field of view aligning with said width of said sample detection area.

20. The improved area array detection readhead of claim 19 wherein said area array detector having an area array with a length and width proportional to about 4×3 and said sample detection having a length and width proportional to said length and width of said area array, said area array detector being positioned such that said length of said area array aligns with said width of said sample detection array and said field being reduced to slightly over half of said sample detection area.

21. An method of improving the spatial resolution of an area array detection readhead for imaging a sample detection area to analyze test samples on said sample detection area, said method comprising the steps of:
    reducing said field of view of said area array detector within said sample detection area to improve the spatial resolution of said area array detector;
    aligning said field of view within said sample detection area;
    shifting said field of view within said sample detection area to cover a first field of said sample detection area; and shifting said field of view within said sample detection area to cover a second field of said sample detection area.

22. The method of claim 21 wherein said first and second portions cover all of said sample detection area.

23. The method of claim 21 wherein said first step of shifting comprises the step of positioning an optical wedge between said area array detector and said sample detection area.

24. The method of claim 23 wherein said second step of shifting comprises the step of changing the position of said optical wedge relative to said area array detector and said sample detection area.

25. The method of claim 21 wherein said step of reducing comprises moving said sample detection area closer to said area array detector to reduce said field to slightly over half of said sample detection area.

26. The method of claim 21 wherein said step of reducing comprises employing a lens with the desired magnification for said area array detector to reduce said field to slightly over half of said sample detection area.

27. The method of claim 24 or 25 wherein sad step of aligning includes rotating said area array detector such that a length of said field of view aligning with said width of said sample detection area.

* * * * *